US008076518B2

(12) United States Patent
Wiggins et al.

(10) Patent No.: US 8,076,518 B2
(45) Date of Patent: *Dec. 13, 2011

(54) CHAIN EXTENDERS

(75) Inventors: Paul L. Wiggins, Baton Rouge, LA (US); John Y. Lee, Baton Rouge, LA (US); Judit Orgad, Baton Rouge, LA (US); David W. Owens, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 990 days.

This patent is subject to a terminal disclaimer.

(21) Appl. No.: 11/534,980

(22) Filed: Sep. 25, 2006

(65) Prior Publication Data
US 2007/0073030 A1 Mar. 29, 2007

Related U.S. Application Data

(63) Continuation-in-part of application No. 11/390,777, filed on Mar. 27, 2006, now Pat. No. 7,288,677.

(60) Provisional application No. 60/665,915, filed on Mar. 28, 2005.

(51) Int. Cl.
*C07C 211/00* (2006.01)
*C08G 18/10* (2006.01)

(52) U.S. Cl. ........ 564/462; 564/461; 564/463; 564/492; 564/498; 564/511; 528/44; 528/52; 528/85; 528/61; 528/62; 528/64; 252/182.2; 252/182.22; 252/182.34

(58) Field of Classification Search .................... 528/61, 528/62, 64, 422, 44, 52, 85; 564/511, 461, 564/462, 463, 492, 498; 252/182.26, 182.2, 252/182.21, 182.22, 182.34
See application file for complete search history.

(56) References Cited

U.S. PATENT DOCUMENTS

| | | |
|---|---|---|
| 2,380,420 A | 7/1945 | Emerson |
| 2,582,128 A | 1/1952 | Hurwitz et al. |
| 2,953,579 A | 9/1960 | Williams et al. |
| 2,965,605 A | 12/1960 | Reynolds et al. |
| 3,209,030 A | 9/1965 | Bicek |
| 3,275,567 A | 9/1966 | Keith et al. |
| 3,336,386 A | 8/1967 | Dovell et al. |
| 3,350,450 A | 10/1967 | Dovell et al. |
| 3,414,616 A | 12/1968 | Summers |
| 3,519,603 A | 7/1970 | Lohse et al. |
| 3,538,161 A | 11/1970 | Dovell |
| 3,609,121 A | 9/1971 | Lohse et al. |
| 3,625,710 A | 12/1971 | Rizzi |
| 3,658,937 A | 4/1972 | Terni et al. |
| 3,761,425 A | 9/1973 | Baessler et al. |
| 3,937,730 A | 2/1976 | Vogel et al. |
| 3,943,158 A | 3/1976 | Dietrich et al. |
| 3,952,056 A | 4/1976 | Vogel et al. |
| 3,994,975 A | 11/1976 | Oude Alink et al. |
| 4,045,486 A | 8/1977 | Krall et al. |
| 4,140,718 A | 2/1979 | Symon |
| 4,161,492 A | 7/1979 | Weissel |
| 4,317,916 A | 3/1982 | Degischer et al. |
| 4,373,107 A | 2/1983 | Tahara et al. |
| 4,521,624 A | 6/1985 | Jackisch |
| 4,528,363 A | 7/1985 | Tominaga |
| 4,631,298 A | 12/1986 | Presswood |
| 4,663,201 A | 5/1987 | House et al. |
| 4,714,512 A | 12/1987 | House et al. |
| 4,760,183 A | 7/1988 | Papenfuhs et al. |
| 4,789,691 A | 12/1988 | Matzke et al. |
| 4,806,616 A | 2/1989 | Baumann et al. |
| 4,900,868 A | 2/1990 | Merten et al. |
| 4,925,974 A * | 5/1990 | Gras .............................. 560/336 |
| 5,001,267 A | 3/1991 | Speranza et al. |
| 5,002,806 A * | 3/1991 | Chung ........................ 427/385.5 |
| 5,008,453 A | 4/1991 | Nalepa et al. |
| 5,041,668 A | 8/1991 | Nalepa et al. |
| 5,145,825 A | 9/1992 | Deeba et al. |
| 5,312,886 A | 5/1994 | House et al. |
| 5,430,188 A | 7/1995 | Bader et al. |
| 5,470,890 A | 11/1995 | House et al. |
| 5,498,585 A | 3/1996 | Bartels et al. |
| 5,591,807 A | 1/1997 | Cai et al. |
| 5,616,799 A | 4/1997 | Planker et al. |
| 5,646,235 A | 7/1997 | Zimmerman et al. |
| 5,744,642 A | 4/1998 | Lantzsch et al. |
| 5,847,067 A | 12/1998 | Gras |

(Continued)

FOREIGN PATENT DOCUMENTS

CA 1218190 A 2/1987

(Continued)

OTHER PUBLICATIONS

Arunajatesan, V., et al., "Optimization of Reductive Alkylation Catalysts by Experimental Design", Organic Reactions Catalysis Society, 2003, pp. 1-6.
De, D., et al., "Polyurethanes With a Diamine-Diamide Chain Extender", Polymer Preprints, 2007, 48(1), 485-486.
Luo, Y., et al., "Response Behavior of an Epoxy Resin/Amine Curing Agent/Carbon Black Composite Film to Various Solvents", Materials Science and Engineering B 139 (2007), pp. 105-113.

(Continued)

*Primary Examiner* — Milton I Cano
*Assistant Examiner* — Michael L Leonard
(74) *Attorney, Agent, or Firm* — James A. Jubinsky

(57) ABSTRACT

This invention provides chain extender compositions. These compositions comprise
(i) an aliphatic secondary diamine, and
(ii) a component selected from the group consisting of:
 (a) a cycloaliphatic primary diamine;
 (b) an aliphatic secondary diamine;
 (c) an aliphatic secondary diamine and an aliphatic primary diamine;
 (d) an aliphatic diimine; and
 (e) a combination of any two or more of (a) through (d), with the proviso that when (ii) is (a), (i) is a noncyclic aliphatic secondary diamine. Processes for producing polyurethanes, polyureas, and polyurea-urethanes are also provided.

18 Claims, No Drawings

U.S. PATENT DOCUMENTS

| | | | |
|---|---|---|---|
| 5,859,164 | A | 1/1999 | Gras et al. |
| 6,013,755 | A | 1/2000 | Primeaux, II et al. |
| 6,156,863 | A | 12/2000 | Wenning |
| 6,218,480 | B1 | 4/2001 | Rappoport |
| 6,399,736 | B1 | 6/2002 | Primeaux, II et al. |
| 6,403,752 | B1 | 6/2002 | House et al. |
| 6,410,004 | B1 * | 6/2002 | Kim et al. ................ 424/70.1 |
| 6,429,338 | B1 | 8/2002 | Burdeniuc et al. |
| 6,444,721 | B2 | 9/2002 | Schwalm et al. |
| 6,803,445 | B2 | 10/2004 | Ishikawa et al. |
| 7,288,677 | B2 | 10/2007 | Lee et al. |
| 7,767,858 | B2 | 8/2010 | Wiggins et al. |
| 2002/0028901 | A1 * | 3/2002 | Gunatillake et al. ............ 528/28 |
| 2003/0004265 | A1 | 1/2003 | Gupta et al. |
| 2003/0036585 | A1 | 2/2003 | Purgett et al. |
| 2004/0015016 | A1 | 1/2004 | Su et al. |
| 2004/0019238 | A1 | 1/2004 | Su et al. |
| 2004/0054150 | A1 | 3/2004 | Murray |
| 2004/0180778 | A1 | 9/2004 | Small |
| 2007/0066786 | A1 | 3/2007 | Hanson, Jr. |
| 2007/0270566 | A1 | 11/2007 | Lee et al. |
| 2008/0004406 | A1 | 1/2008 | Lee et al. |
| 2008/0194788 | A1 | 8/2008 | Lee et al. |

FOREIGN PATENT DOCUMENTS

| | | |
|---|---|---|
| CN | 1352202 | 6/2002 |
| CN | 1939949 A | 4/2007 |
| DE | 1163315 | 2/1964 |
| DE | 2940738 A1 | 4/1981 |
| DE | 3728141 | 3/1989 |
| DE | 102005046641 A1 | 4/2007 |
| EP | 0014985 A1 | 9/1980 |
| EP | 0288067 A1 | 10/1988 |
| EP | 0309980 A1 | 4/1989 |
| EP | 0420426 A2 | 4/1991 |
| EP | 0469751 A1 | 2/1992 |
| EP | 0688802 A1 | 12/1995 |
| EP | 0779278 A3 | 6/1997 |
| EP | 1067116 A1 | 1/2001 |
| EP | 1229020 A1 | 8/2002 |
| EP | 0802209 B1 | 4/2003 |
| GB | 1070759 | 6/1967 |
| GB | 1320863 | 6/1973 |
| GB | 1478446 | 6/1977 |
| JP | 63052146 A2 | 3/1988 |
| JP | 5274914 A2 | 10/1993 |
| JP | 09100260 A | 4/1997 |
| SU | 387551 | 3/1973 |
| WO | WO-92/18575 A1 | 10/1992 |
| WO | WO-97/01529 | 1/1997 |
| WO | WO-00/26181 A1 | 5/2000 |
| WO | WO-02/102869 A1 | 12/2002 |
| WO | WO-03/018531 A1 | 3/2003 |
| WO | WO-2004/073634 A2 | 9/2004 |
| WO | WO-2005/033119 | 4/2005 |
| WO | WO-2006/028728 A1 | 3/2006 |
| WO | WO-2006/104528 A1 | 10/2006 |

OTHER PUBLICATIONS

Mylroie, Victor L., et al., "Reductive Alkylation Optimized by Techniques of Experimental Design", Catalysis of Organic Reactions, Chem. Ind. Series, vol. 68, Marcel Dekker, New York, 1996, pp. 301-312.

Wang et al., "Bolaamphiphilic Single-Chain Bis-Schiff Base Derivatives: Aggregation and Thermal Behavior in Aqueous Solution." Langmuir, 2001, vol. 17, p. 3162-3167.

Arunajatesan, V., et al., "Optimization of Reductive Alkylation Catalysts by Experimental Design", Chemical Industries (CRC Press), vol. 115, Catalysis of Organic Reactions), 2007, pp. 481-487.

Adams et al., "Restricted Rotation in Aryl Amines. XIV. Isopropyl Derivatives of Dibenzenesulfonamidomesitylene", J. Am. Chem. Soc., 1950, pp. 5077-5079, vol. 72.

Barmetter, "Acid-Catalyzed [3.3]-Sigmatropic Rearrangements of N-Propargylanilines", Helvetica Chimica Acta, 1990, pp. 1515-1573, vol. 73, Verlag Helvetica Chimica Acta, Basel, CH.

Billaud et al., "Quantitative Analysis of Epoxy Resin Cure Reaction: A Study by Near-Infrared Spectroscopy", Applied Spectroscopy, 2002, pp. 1413-1421, vol. 56(11).

Campbell et al., "The Preparation of Unsymmetrical Secondary Aliphatic Amines", J. Am. Chem. Soc., 1944, pp. 82-84, vol. 66.

Childs et al., "Assembly of a Nanoscale Chiral Ball Through Supramolecular Aggregation of Bowl-Shaped Triangular Helicates", Angewandte Chemie, 2002, pp. 4244-4247, vol. 41, VCH Verlagsgesellschaft, Weinheim, DE.

Childs et al., "Using Noncovalent Intra-strand and Inter-strand Interactions to Prescribe Helix Formation within a Metallosupramolecular System", Chem. Eur. J., 2004, pp. 4291-4300, vol. 10(17).

Deschenaux et al., "Structural Isomerism in Polycondensates. IV. Synthesis and Characterization of Liquid Crystalline Poly(azomethines) and Low Molecular Weight Model Compounds", Helvetica Chimica Acta, 1986, pp. 1349-1355, vol. 69(6).

Distefano, "Reinvestigation of the Formaldehyde-Aniline Condensation. Part 4. Ultraviolet Photoelectron and Electron Transmission Spectra of N-Methyleneaniline and its Symmetric Dimethyl Ring-substituted Homologues and Semiempirical Theoretical Evaluations", J. Chem. Soc. Perkin Trans II, 1985, pp. 1623-1627.

Dovell & Greenfield, "Platinum Metal Sulfides as Heterogeneous Hydrogenation Catalysts", J. Am. Chem. Soc., 1965, pp. 2767-2768, vol. 87.

Dvolaitzky et al., "Stable N,N'-di-tert-butyl-meta-phenylenebisnitroxides-Unexpected Ground-State Singlets", Angewandte Chemie Int. Ed. Engl., 1992, pp. 180-181, vol. 31(2).

Emerson et al., "The Reductive Alkylation of Hindred Aromatic Primary Amines", J. Am. Chem. Soc., 1941, pp. 972-974, vol. 63.

Hine et al., "Polar Effects on the Formation of Imines from Isobutyraldehyde and Primary Aliphatic Amines", The Journal of Organic Chemistry, 1970, pp. 340-344, vol. 85.

Jie et al., "Bridged Bis-Pyridinylimino Dinickel (II) Complexes: Syntheses, Characterization, Ethylene Oligomerization and Polymerization", Journal of Organometallic Chemistry, 2005, pp. 1739-1749, vol. 690, Elsevier-Sequoia S.A. Lausanne, CH.

Lai, J.T., "Ketoform Reaction. Synthesis of Hindered Imines from 2,6-dialkylanilines and Ketones", Tetrahedron Letters, 2002, p. 1965-1967; 1996, vol. 43, Elsevier Science Publishers, Amsterdam, NL.

Layer, Robert W.; "The Chemistry of Imines", Chemical Reviews; 1963; vol. 63; pp. 489-510.

Luo et al., "New Bi-nuclear and Multi-nuclear α-diimine/nickel Catalysts for Ethylene Polymerization", Journal of Molecular Catalysts, 2005, pp. 153-161, vol. 227.

March, "Reactions, Mechanisms, and Structure", Advanced Organic Chemistry, 1992, pp. 896-900, 4$^{th}$ Ed., John Wiley & Sons, US.

Mi et al., "Homo- and Copolymerization of Norbornene and Styrene with Pd- and Ni-Based Novel Bridged Dinuclear Diimine Complexes and MAO",Macromol. Chem. Phys., 2003, pp. 868-876, vol. 204(5/6).

Pal et al., "Schiff Base Linked Ferrocenyl Complexes for Second-Order Nonlinear Optics", Journal of Organometallic Chemistry, 2000, pp. 248-259, vol. 604, Elsevier-Sequoia S.A., Lausanne, CH.

Parker, et al., "Reaction Chemistry of Tri-Substituted Mesitylene derivatives and the Synthesis of Sterically Buttressed 1,3,5-triaminocyclohexyl Ligands", J. Chem. Soc., Perkin Transactions 2, Chemical Society, 1997, pp. 1445-1452.

Patai, The Chemistry of the Carbon-Nitrogen Double Bond, 1970, pp. 61-67, 130, 255-256, 276-293, 296-298, Interscience Publishers, Great Britain.

Perez, Jr. et al., "Performance and Processing Enhancements of Aromatic Polyurea Elastomer Systems Prepared from High 2,4'-MDI Isocyanates", Huntsman Corporation; 3 pages.

Posey et al., "New Secondary Amine Chain Extenders for Aliphatic Polyurea Materials", Polyurea Development Association 2003 Annual Conference, Aug. 19-21, 2003, John Ascuaga's Nugget Casino Resort, Reno, NV; 11 pages.

Rylander, "Reduction Alkylation", Catalytic Hydrogenation in Organic Syntheses, 1979, pp. 165-174, Academic Press, New York, NY, USA.

Smith et al., "Preparation of Polyimides Utilizing the Diels-Alder Reaction. 1,4-N,N'-Bis(Butadienyl-2-Methyl) Diamido)-2,3,5,6-tetramethylbenzenes with Bismaleimides", Macromolecules, American Chemical Society, 1996, pp. 1123-1130, vol. 29, Easton, US.

Sun et al., "Supramolecular Helical Architecture Assembled by Double-Helical [$Ag_2L_2$] Units", Journal of Organometallic Chemistry, 2004, pp. 43-49, vol. 689.

Taneda et al., "Photochromism of Polymorphic 4, 4'-methylenebis-(N-salicylidene-2, 6-diisopropylaniline) Crystals", Org. Biomol. Chem., 2004, pp. 499-504, vol. 2(4).

Trost et al., "Dehydrogenation of Amines. An approach to Imines and Aldehydes", The Journal of Organic Chemistry, 1981, pp. 4617-4620, vol. 46.

Voigt-Martin et al., "Structure and Defects in Sanidic Liquid Crystalline Polymers. 2. Structure Analysis of Sanidic Polymers by Simulation of Diffraction Patterns From Monomeric Analogs", Macromolecules, 1995, pp. 243-254, vol. 28(1).

Caplus Abstract of Vasilenko et al., "Electron Spectra and Structure of Molecules Containing a Carbon:Nitrogen Group. II. Absorption Spectra of Benzyideneaniline Derivatives and Bis(azomethines)", Zhurnal Fizicheskoi Khimii; 1976; 50(3(; pp. 597-601; Accession No. 1976:405028.

Caplus Abstract of Zhang et al., "Synthesis of Bis(salicylaldininato) Nickel Complexes and Their Catalytic Behavior for Vinyl Polymerization of Norbornene"; Gaofenzi Xuebao; 2004; (5); pp. 758-762; Accession No. 2004:985377.

Johnson Matthey Catalysts & Chemicals Division, Heterogeneous Catalyst Application Table.

Shepherd, R. G., et al., "Antituberculous Agents. II. N,N'-Diisopropylethylenediamine and Analogs", Journal of Medicinal & Pharmaceutical Chemistry, 1962, vol. 5, pp. 823-835.

* cited by examiner

CHAIN EXTENDERS

REFERENCE TO RELATED APPLICATIONS

This application is a continuation-in-part of U.S. application Ser. No. 11/390,777, filed Mar. 27, 2006, which in turn claims the priority of U.S. Provisional Application No. 60/665,915, filed Mar. 28, 2005, the disclosures of which are incorporated herein by reference.

TECHNICAL FIELD

This invention relates to the use of aliphatic diamines to form polyurethanes, polyureas, and polyurea-urethanes.

BACKGROUND

There are many polyfunctional compounds, including diols and aromatic diamines, which are indicated to be useful as chain extenders in the preparation of polyurethane, polyurea, and polyurethane-urea polymers and/or as curing agents for epoxy resins. None of these compounds has a reactivity such as to make it universally ideal, and many fail to provide satisfactory properties in the products made by their use. Thus, there is still a need to find compounds capable of serving as chain extenders or curing agents. U.S. Pat. No. 4,806,616 teaches the use of certain N,N'-dialkylphenylenediamines as chain extenders in preparing polyurethanes and polyureas. In this connection, also see for example U.S. Pat. No. 4,528,363, which teaches the use of secondary aliphatic diamines as part of a resin binder, and U.S. Pat. No. 6,218,480 B1, which discloses use of aromatic diamines as hardeners for polyurethanes. Secondary aromatic diamines have also been used as anti-degradants for rubber; see U.S. Pat. No. 4,900,868.

There is a growing need for chain extenders with slower cure rates, so it would be a further advantage if aliphatic diamines exhibited slower curing rates than those of presently available chain extenders.

SUMMARY OF INVENTION

This invention in part provides chain extenders which are mixtures of aliphatic secondary diamines and one or more other components. These mixtures, when included in formulations for polyurethanes, polyureas, and polyurea-urethanes, produce such polymers at desired cure rates and having desirable physical properties.

One embodiment of this invention provides a chain extender composition. The composition comprises (i) an aliphatic secondary diamine and (ii) another component. The component is selected from the group consisting of:
  (a) a cycloaliphatic primary diamine;
  (b) an aliphatic secondary diamine;
  (c) an aliphatic secondary diamine and an aliphatic primary diamine;
  (d) an aliphatic diimine; and
  (e) a combination of any two or more of (a) through (d),
with the proviso that when (ii) is (a), (i) is a noncyclic aliphatic secondary diamine.

Another embodiment of this invention is a process for producing a polymer which is a polyurethane, polyurea, or polyurea-urethane. The process comprises mixing together (A) at least one aliphatic polyisocyanate, (B) at least one polyol and/or at least one polyetheramine, and (C) a chain extender comprised of (i) an aliphatic secondary diamine and (ii) another component. The component is selected from the group consisting of:
  (a) a cycloaliphatic primary diamine;
  (b) an aliphatic secondary diamine;
  (c) an aliphatic secondary diamine and an aliphatic primary diamine;
  (d) an aliphatic diimine; and
  (e) a combination of any two or more of (a) through (d),
with the proviso that when (ii) is (a), (i) is a noncyclic aliphatic secondary diamine.

Still another embodiment of this invention is a polymer which is a polyurethane, polyurea, or polyurea-urethane, which polymer is formed from ingredients comprising (A) at least one aliphatic polyisocyanate, (B) at least one polyol and/or at least one polyetheramine, and (C) a chain extender comprised of (i) an aliphatic secondary diamine and (ii) another component. The component is selected from the group consisting of:
  (a) a cycloaliphatic primary diamine;
  (b) an aliphatic secondary diamine;
  (c) an aliphatic secondary diamine and an aliphatic primary diamine;
  (d) an aliphatic diimine; and
  (e) a combination of any two or more of (a) through (d),
with the proviso that when (ii) is (a), (i) is a noncyclic aliphatic secondary diamine.

These and other embodiments and features of this invention will be still further apparent from the ensuing description and appended claims.

FURTHER DETAILED DESCRIPTION OF THE INVENTION

Chain Extender Compositions of the Invention

Chain extender compositions of this invention are made up of an aliphatic secondary diamine and one or more other components selected from (a) at least one cycloaliphatic primary diamine, wherein said aliphatic secondary diamine of (i) is a noncyclic diamine; (b) at least one aliphatic secondary diamine; (c) an aliphatic secondary diamine and an aliphatic primary diamine; and (d) an aliphatic diimine. Preferred components for use with the aliphatic secondary diamine are cycloaliphatic primary diamines. The components can be present in the chain extender composition in a variety of proportions; the preferred ratios vary with the type of component from (ii).

I. Component (i)

Aliphatic secondary diamines are component (i) of the chain extender compositions of the invention. The aliphatic secondary diamines are hydrocarbyl secondary diamines where the hydrocarbyl portion of the diamine is aliphatic, where "hydrocarbyl portion" refers to the moiety to which the amino groups are bound. The hydrocarbyl portion of the aliphatic diamine can be cyclic, branched, or, preferably, straight chain. The amino hydrocarbyl groups of the aliphatic secondary diamine can be cyclic, branched, or straight chain. Preferably, the amino hydrocarbyl groups are straight chain or, more preferably, branched chain alkyl groups having from three to about twelve carbon atoms. Examples of suitable amino hydrocarbyl groups include ethyl, propyl, isopropyl, n-butyl, sec-butyl, t-butyl, pentyl, cyclopentyl, hexyl, methylcyclohexyl, heptyl, octyl, cyclooctyl, nonyl, decyl, dodecyl, and the like. Preferably, the aliphatic secondary diamine has about eight to about forty carbon atoms; more preferably, the aliphatic secondary diamine has about ten to about thirty carbon atoms. Particularly preferred aliphatic secondary diamines have cyclic or straight chain hydrocarbyl portions and have about twelve to about twenty-five carbon atoms.

Aliphatic secondary diamines that can be used in this invention include, but are not limited to, N,N'-diisopropylethylenediamine, N,N'-di-sec-butyl-1,2-diaminopropane, N,N'-di(2-butenyl)-1,3-diaminopropane, N,N'-di(1-cyclopropylethyl)-1,5-diaminopentane, N,N'-di(3,3-dimethyl-2-butyl)-1,5-diamino-2-methylpentane, N,N'-di-sec-butyl-1,6-diaminohexane, N,N'-di(3-pentyl)-2,5-dimethyl-2,5-hexanediamine, N,N'-di(4-hexyl)-1,2-diaminocyclohexane, N,N'-dicyclohexyl-1,3-diaminocyclohexane, N,N'-di(1-cyclobutylethyl)-1,4-diaminocyclohexane, N,N'-di(2,4-dimethyl-3-pentyl)-1,3-cyclohexanebis(methylamine), N,N'-di(1-penten-3-yl)-1,4-cyclohexanebis(methylamine), N,N'-diisopropyl-1,7-diaminoheptane, N,N'-di-sec-butyl-1,8-diaminooctane, N,N'-di(2-pentyl)-1,10-diaminodecane, N,N'-di(3-hexyl)-1,12-diaminododecane, N,N'-di(3-methyl-2-cyclohexenyl)-1,2-diaminopropane, N,N'-di(2,5-dimethylcyclopentyl)-1,4-diaminobutane, N,N'-di(isophoryl)-1,5-diaminopentane, N,N'-di(menthyl)-2,5-dimethyl-2,5-hexanediamine, N,N'-di(undecyl)-1,2-diaminocyclohexane, N,N'-di-2-(4-methylpentyl)-isophoronediamine, and N,N'-di(5-nonyl)-isophoronediamine. A preferred aliphatic secondary diamine is N,N'-di-(3,3-dimethyl-2-butyl)-1,6-diaminohexane.

II. Component (ii)

Component (ii) is selected from the group consisting of (a) a cycloaliphatic primary diamine; (b) an aliphatic secondary diamine; (c) an aliphatic secondary diamine and an aliphatic primary diamine; (d) an aliphatic diimine; and (e) a combination of any two or more of (a) through (d), with the proviso that when (ii) is (a), (i) is a noncyclic aliphatic secondary diamine. Thus mixtures of subcomponents (a)-(d) in various combinations are within the scope of this invention.

Subcomponent (a)

Cycloaliphatic primary diamines are subcomponent (a) of component (ii). When component (ii) is a cycloaliphatic primary diamine, the aliphatic secondary diamine of component (i) is a noncyclic aliphatic secondary diamine. Noncyclic aliphatic secondary diamines are aliphatic secondary diamines as described above the two amino groups are not bound to a cycloaliphatic group or via a substituent of a cycloaliphatic group. A preferred noncyclic aliphatic secondary diamine is N,N'-di-(3,3-dimethyl-2-butyl)-1,6-diaminohexane.

The cycloaliphatic primary diamines used in this invention are hydrocarbyl primary diamines in which the two amino groups are bound to a cycloaliphatic group. The cycloaliphatic group can be a single ring, fused rings, bicyclic rings, or a tricyclic system (which tricyclic system can contain fused rings and/or bicyclic rings). Single rings are preferred. The amino groups may be bound directly to the ring, or one or both amino groups may be bound to a group that is a substituent of the ring. It is preferred that at least one of the amino groups is bound to the ring. Preferably, the cycloaliphatic secondary diamine has about six to about forty carbon atoms; more preferably, the aliphatic secondary diamine has about ten to about twenty-five carbon atoms. The relative proportions of aliphatic secondary diamine to cycloaliphatic primary diamine in the chain extender composition are preferably about 10:1 to about 1:1 on a weight basis; more preferably, the relative proportions on a weight basis are about 5:1 to about 1:1. Even more preferred are relative proportions on a weight basis of about 3:1 to about 1:1.

Cycloaliphatic primary diamines that are suitable in the practice of this invention include, but are not limited to, 1,2-diaminocyclohexane, 1,3-diaminocyclohexane, 1,4-diaminocyclohexane, 2,4-diethyl-6-methyl-1,3-cyclohexanediamine, 4,6-diethyl-2-methyl-1,3-cyclohexanediamine, 1,3-cyclohexanebis(methylamine), 1,4-cyclohexanebis(methylamine), isophorone diamine, bis(p-aminocyclohexyl)methane, bis(3-methyl-4-aminocyclohexyl)methane, 1,8-diamino-p-menthane, and 3(4),8(9)-bis-(aminomethyl)-tricyclo[5.2.1.0(2,6)]decane (TCD diamine; also called octahydro-4,7-methanoinden-1(2),5(6)-dimethanamine or octahydro-4,7-methano-1H-indenedimethyl-amine). Preferred cycloaliphatic primary diamines include isophorone diamine.

A preferred chain extender composition, when component (ii) is a cycloaliphatic primary diamine in which the cycloaliphatic group has a single ring, and/or at least one of the amino groups is bound directly to a ring of the cycloaliphatic primary diamine, has relative proportions of (i) to (ii) on a weight basis of about 5:1 to about 1:1.

Subcomponent (b)

Aliphatic secondary diamines are subcomponent (b) of component (ii), and suitable aliphatic secondary diamines for subcomponent (c) and preferences therefor are as described above for component (i). The aliphatic secondary diamines can be in any suitable proportion relative to each other.

When (ii) is an aliphatic secondary diamine, a preferred chain extender composition in this invention is one in which one of the aliphatic secondary diamines is N,N'-di-(3,3-dimethyl-2-butyl)-1,6-diaminohexane.

Subcomponent (c)

An aliphatic secondary diamine and an aliphatic primary diamine are subcomponent (c) of (ii). The aliphatic secondary diamine and the aliphatic primary diamine can be in any suitable proportion relative to each other, and their combined total amount can be in any relative proportion to the aromatic primary diamine of (i). Preferably, the proportion of the combined total amount of aliphatic secondary diamine and aliphatic primary diamine relative to the aromatic primary diamine of (i) is in the range of about 0.5:1 to about 1:0.5.

Suitable aliphatic secondary diamines for subcomponent (c) and preferences therefor are as described above for component (i). When the aliphatic primary diamine of subcomponent (c) is a cycloaliphatic primary diamine, suitable compounds and preferences are as described above for subcomponent (a). When the aliphatic primary diamine of subcomponent (c) is a noncyclic aliphatic primary diamine, it can be branched or, preferably, a straight chain. Preferably, the aliphatic primary diamine has about four to about thirty carbon atoms; more preferably, the aliphatic primary diamine has about six to about twenty carbon atoms.

Examples of noncyclic aliphatic primary diamines that can be used as part of subcomponent (c), include, but are not limited to, ethylenediamine, 1,2-diaminopropane, 1,3-diaminopropane, 1,4-diaminobutane, 1,5-diaminopentane, 1,5-diamino-2-methylpentane, 1,6-diaminohexane, 2,5-dimethyl-2,5-hexanediamine, 1,7-diaminoheptane, 1,8-diaminooctane, 1,10-diaminodecane, and 1,12-diaminododecane.

When (ii) is an aliphatic secondary diamine and an aliphatic primary diamine, a preferred chain extender composition in this invention is one in which one of the aliphatic secondary diamines is N,N'-di-(3,3-dimethyl-2-butyl)-1,6-diaminohexane.

Subcomponent (d)

Aliphatic diimines (diimines are also called diketimines) are subcomponent (d) of component (ii). Processes for forming diimines from primary diamines are provided in commonly-owned copending U.S. patent application Ser. No. 11/390,777, filed Mar. 27, 2006, and PCT Application No.

PCT/US2005/47696, filed Dec. 30, 2005. Other disclosures of methods for making diimines include WO 97/01529, and U.S. Pat. No. 4,855,500, and U.S. Pat. No. 4,536,518.

The hydrocarbyl portion of the aliphatic diimine can be cyclic, branched, or straight chain hydrocarbyl group, where "hydrocarbyl portion" refers to the moiety to which the imino groups are bound. Preferably, the aliphatic diimine has about six to about forty carbon atoms; more preferably, the aliphatic diimine has about ten to about thirty carbon atoms. The hydrocarbylidene groups of the imino groups of the aliphatic diimine generally have from one to about twenty carbon atoms; the hydrocarbylidene groups may be straight chain, branched, or cyclic. Preferably, the imino hydrocarbylidene groups are straight chain or branched chain alkylidene groups having from three to about six carbon atoms. Examples of suitable imino hydrocarbylidene groups include ethylidene, propylidene, isopropylidene, 1-cyclopropylethylidene, n-butylidene, sec-butylidene, cyclobutylidene, 2-ethylbutylidene, 3,3-dimethyl-2-butylidene, 3-pentylidene, 3-penten-2-ylidene, cyclopentylidene, 2,5-dimethylcyclopentylidene, 2-cyclopentenylidene, hexylidene, methylcyclohexylidene, menthylidene, ionylidene, phorylidene, isophorylidene, heptylidene, 2,6,-dimethyl-3-heptylidene, cyclooctylidene, 5-nonylidene, decylidene, 10-undecenylidene, and the like.

Aliphatic diimines that can be used in this invention include, but are not limited to, N,N'-diisopropylidene-ethylenediamine, N,N'-di-sec-butylidene-1,2-diaminopropane, N,N'-di(2-butenylidene)-1,3-diaminopropane, N,N'-di(1-cyclopropylethylidene)-1,5-diaminopentane, N,N'-di(3,3-dimethyl-2-butylidene)-1,5-diamino-2-methylpentane, N,N'-di-sec-butylidene-1,6-diaminohexane, N,N'-di(3-pentylidene)-2,5-dimethyl-2,5-hexanediamine, N,N'-di(4-hexylidene)-1,2-diaminocyclohexane, N,N'-dicyclohexylidene-1,3-diaminocyclohexane, N,N'-di(1-cyclobutylethylidene)-1,4-diaminocyclohexane, N,N'-di(2,4-dimethyl-3-pentylidene)-1,3-cyclohexanebis(methylamine), N,N'-di(1-penten-3-ylidene)-1,4-cyclohexanebis(methylamine), N,N'-diisopropylidene-1,7-diaminoheptane, N,N'-di-sec-butylidene-1,8-diaminooctane, N,N'-di(2-pentylidene)-1,10-diaminodecane, N,N'-di(3-hexylidene)-1,12-diaminododecane, N,N'-di(3-methyl-2-cyclohexenylidene)-1,2-diaminopropane, N,N'-di(2,5-dimethylcyclopentylidene)-1,4-diaminobutane, N,N'-di (isophorylidene)-1,5-diaminopentane, N,N'-di (menthylidene)-2,5-dimethyl-2,5-hexanediamine, N,N'-di (undecylidene)-1,2-diaminocyclohexane, N,N'-di-2-(4-methylpentylidene)-isophoronediamine, and N,N'-di(5-nonylidene)-isophoronediamine.

Processes of the Invention

In the processes of the invention, a polymer which is a polyurethane, polyurea, or polyurea-urethane is made by mixing together at least one aliphatic polyisocyanate, at least one polyol and/or at least one polyetheramine, and a chain extender composition of the invention. As is well known in the art, other components may also be included when making the polyurethane, polyurea, or polyurethane-urea, such as one or more flame retardants, thermal stabilizers, and/or surfactants. In some processes of the invention, the polyol or polyetheramine, chain extender composition, and when used, optional ingredients, are blended together to form a first mixture, followed by blending this first mixture with the isocyanate to form a second mixture; this second mixture is allowed to cure. In other processes of this invention, the isocyanate and the polyol or polyetheramine are blended together to form a prepolymer, which prepolymer is then mixed together with the chain extender composition to form the desired polymer. In still other processes of the invention, the isocyanate is mixed with polyol or polyetheramine to form a quasiprepolymer; polyol or polyetheramine is mixed with the chain extender composition to form a mixture; and then the mixture is mixed with the quasiprepolymer to form the desired polymer. Thus, the chain extender composition is reacted with an aliphatic polyisocyanate and at least one polyol and/or at least one polyetheramine or with a prepolymer or a quasiprepolymer of the isocyanate and the polyol or polyetheramine. In the practice of this invention, use of quasiprepolymers is preferred way of producing polyureas.

The aliphatic polyisocyanates are organic polyisocyanates having at least two isocyanate groups. Generally, the isocyanates have a free —NCO content of at least about 0.1% by weight. Aliphatic polyisocyanates that can be used in the practice of this invention include isophorone diisocyanate (IPDI), cyclohexylene diisocyanate, 4,4'-methylenedicyclohexyl diisocyanate (H12MDI); mixed aralkyl diisocyanates including tetramethylxylyl diisocyanates; and polymethylene isocyanates including 1,4-tetramethylene diisocyanate, 1,5-pentamethylene diisocyanate, 1,6-hexamethylene diisocyanate (HMDI), 1,7-heptamethylene diisocyanate, 2,2,4- and 2,4,4-trimethylhexamethylene diisocyanate, 1,10-decamethylene diisocyanate, and 2-methyl-1,5-pentamethylene diisocyanate. A preferred aliphatic polyisocyanate is isophorone diisocyanate (IPDI). Examples of isocyanates that can be used are also taught in, for example, U.S. Pat. No. 4,595,742.

Isocyanate-reactive polyols and polyetheramines (sometimes referred to as amine-terminated polyols) that are typically used in making polyurethanes, polyureas, and polyurea-urethanes range in molecular weight from about 60 to over 6,000. The polyols can be dihydric, trihydric, or polyhydric polyols, but are usually dihydric. Examples of suitable polyols include poly(ethyleneoxy) glycols, dipropylene glycol, poly(propyleneoxy) glycols, dibutylene glycol, poly(butyleneoxy) glycols, and the polymeric glycol from caprolactone, commonly known as polycaprolactone. The polyetheramines used to make polyurethanes, polyureas, and polyurea-urethanes are amine-capped polyols which are the reaction product of a polyol and then an amine with alkylene oxides as well as amine-capped hydroxyl-containing polyesters. Polyetheramines typically have a molecular weight of about 200 to about 6000. Several commercially available polyetheramines known as Jeffamines® available from Huntsman Chemical Company and include Jeffamine® T-5000, a polypropylene oxide triamine of about 5000 molecular weight, XTJ-509, a polypropylene oxide triamine of about 3000 molecular weight, XTJ-510, a polypropylene oxide diamine of about 4000 molecular weight, and Jeffamine® D-2000, a polypropylene oxide diamine of about 2000 molecular weight. Jeffamine® T-5000 and Jeffamine® D-2000 are preferred polyetheramines in the practice of this invention.

In a preferred process of the invention, component (i) of the chain extender composition is N,N'-di-(3,3-dimethyl-2-butyl)-1,6-diaminohexane. In another preferred process of the invention, component (i) of the chain extender composition is isophorone diamine.

Polymers Formed by the Invention

The polymers formed by the invention are polyurethanes, polyureas, and polyurea-urethanes (sometimes called polyurea-polyurethanes). Because of their differing gel times (cure rates), these polymers can be used in different applications. Polyurethanes, polyureas, and polyurea-urethanes made with the chain extender compositions of the invention have more desirable gel times, and, at a minimum, the physical properties of the polymers are not adversely affected by the use of the chain extender compositions of the invention. In fact, a stiffer polymer is obtained when made from chain extender compositions of the invention in comparison to polymers made with the individual chain extenders.

A preferred polymer formed by this invention is formed from a chain extender composition of the invention in which component (i) is an aliphatic secondary diamine is N,N'-di-(3,3-dimethyl-2-butyl)-1,6-diaminohexane, or is formed from a chain extender composition in which component (ii) is isophorone diamine.

Another preferred polymer formed by this invention is formed from isophorone diisocyanate, at least one polyetheramine, and a chain extender composition in which component (i) is an aliphatic secondary diamine in which the hydrocarbyl portion of the diamine is a straight chain, and/or has amino hydrocarbyl groups which are straight chain or branched chain alkyl groups, and/or is an aliphatic secondary diamine having about 10 to about thirty carbon atoms, and in which component (ii) is a cycloaliphatic primary diamine in which the cycloaliphatic group has a single ring and/or one of the amino groups is bound directly to a ring.

The following example is presented for purposes of illustration, and is not intended to impose limitations on the scope of this invention.

In the following Example, the isocyanate was isophorone diisocyanate (IPDI). Jeffamine® D-2000 (a polyetheramine, Huntsman Chemical) was used to make the polyureas. The aliphatic secondary diamine was N,N'-di-(3,3-dimethyl-2-butyl)-1,6-diaminohexane. A pneumatic dispensing gun (DP-400-85-1, Mixpac Systems AG, Switzerland) was used in conjunction with a static mixer. The static mixer was either a plastic spiral bell mixer with 30 elements and an inner diameter of 0.37 inches (EA 370-30, Ellsworth Adhesives) or a plastic bell mixer with 48 elements and an inner diameter of 0.25 inches (Statomix® MS 06-48).

Example 1

Polyurea formulations containing isocyanate, Jeffamine® D-2000 an aliphatic secondary diamine, and a cycloaliphatic primary diamine were prepared. The isocyanate was mixed together with a portion of the Jeffamine® D-2000 to form a quasiprepolymer. The remainder of the Jeffamine® D-2000 was blended with the chain extender(s) to form a mixture. This mixture was then added to one compartment of the pneumatic mixing gun; the quasiprepolymer was added to the other compartment. The mixture and quasiprepolymer were mixed (reacted) by pushing them through a static mixer onto a steel plate and cured at room temperature. One polyurea was prepared without a cycloaliphatic primary diamine for comparative purposes. Amounts of the chain extenders relative to each other (by weight) are listed in Table 1. The cured polymers were subjected to testing. Properties of the polyureas are summarized in Table 1.

TABLE 1

|  | Comparative | Run 1 | Run 2 |
| --- | --- | --- | --- |
| N,N'-di-(3,3-dimethyl-2-butyl)-1,6-diaminohexane | 47.1 | 34.9 | 28.3 |
| Isophorone diamine | — | 6.2 | 9.3 |
| Gel time (cure rate) | 305 sec | 162 sec | 86 sec |
| Shore D hardness, 0 sec. | 49 | 48 | 48 |
| Shore D hardness, 10 sec. | 45 | 44 | 43 |
| Tensile strength | 2480 psi | 2270 psi | 2340 psi |
| Elongation | 510% | 380% | 390% |
| Modulus (100%) | 1100 psi | 1230 psi | 1310 psi |
| Modulus (300%) | 1540 psi | 1890 psi | 2110 psi |
| Tear strength | 520 pli | 550 pli | 550 pli |

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation in its practice.

The invention claimed is:

1. A chain extender composition which comprises
   (i) N,N'-di-(3,3-dimethyl-2-butyl)-1,6-diaminohexane, and
   (ii) a cycloaliphatic primary diamine,
wherein the relative proportions of N,N'-di-(3,3-dimethyl-2-butyl)-1,6-diaminohexane to cycloaliphatic primary diamine in the chain extender composition are in the range of about 5.7:1 to about 3:1 on a weight basis.

2. A composition as in claim 1 wherein (ii) is a cycloaliphatic primary diamine which has at least one of the following features:
   the cycloaliphatic group has a single ring;
   at least one of the amino groups is bound directly to a ring.

3. A composition as in claim 2 wherein said cycloaliphatic primary diamine is isophorone diamine.

4. A process for producing a polymer, which process comprises mixing together (A) at least one aliphatic polyisocyanate, (B) at least one polyol and/or at least one polyetheramine, and (C) a chain extender comprised of
   (i) N,N'-di-(3,3-dimethyl-2-butyl)-1,6-diaminohexane, and
   (ii) a cycloaliphatic primary diamine,
wherein the relative proportions of N,N'-di-(3,3-dimethyl-2-butyl)-1,6-diaminohexane to cycloaliphatic primary diamine in the chain extender composition are in the range of about 5.7:1 to about 3:1 on a weight basis.

5. A process as in claim 4 wherein said polyisocyanate is isophorone diisocyanate.

6. A process as in claim 4 wherein (B) is at least one polyetheramine.

7. A process as in claim 4 wherein said polyisocyanate is isophorone diisocyanate, and wherein (B) is at least one polyetheramine.

8. A process as in claim 4 wherein (ii) is isophorone diamine.

9. A process as in claim 4 wherein (ii) is a cycloaliphatic primary diamine which has at least one of the following features:

the cycloaliphatic group has a single ring;

one of the amino groups is bound directly to a ring.

10. A process as in claim 9 wherein said polyisocyanate is isophorone diisocyanate, and wherein (B) is at least one polyetheramine.

11. A process as in claim 4 wherein a quasiprepolymer is formed during the process.

12. A process as in claim 4 wherein a prepolymer is formed during the process.

13. A polymer formed from ingredients comprising (A) at least one aliphatic polyisocyanate, (B) at least one polyol and/or at least one polyetheramine, and (C) a chain extender comprised of (i) N,N'-di-(3,3-dimethyl-2-butyl)-1,6-diaminohexane, and (ii) a cycloaliphatic primary diamine, wherein the relative proportions of N,N'-di-(3,3-dimethyl-2-butyl)-1,6-diaminohexane to cycloaliphatic primary diamine in the chain extender composition are in the range of about 5.7:1 to about 3:1 on a weight basis.

14. A polymer as in claim 13 wherein said polyisocyanate is isophorone diisocyanate.

15. A polymer as in claim 13 wherein (B) is at least one polyetheramine.

16. A polymer as in claim 13 wherein said polyisocyanate is isophorone diisocyanate, and wherein (B) is at least one polyetheramine.

17. A polymer as in claim 13 wherein (ii) is a cycloaliphatic primary diamine which has at least one of the following features:

the cycloaliphatic group has a single ring;

one of the amino groups is bound directly to a ring.

18. A polymer as in claim 13 wherein (ii) is isophorone diamine.

\* \* \* \* \*